United States Patent [19]

Ogden

[11] Patent Number: 5,656,016
[45] Date of Patent: Aug. 12, 1997

[54] SONOPHORETIC DRUG DELIVERY SYSTEM

[75] Inventor: John E. Ogden, Bend, Oreg.

[73] Assignee: Abbott Laboratories, Abbott Park, Ill.

[21] Appl. No.: 576,821

[22] Filed: Mar. 18, 1996

[51] Int. Cl.$^6$ .............................. A61H 1/00; A61B 17/20
[52] U.S. Cl. ............................. 601/2; 604/22; 604/290
[58] Field of Search .............................. 604/20, 22, 290; 128/660.01, 660.03; 601/2, 17

[56] References Cited

U.S. PATENT DOCUMENTS

| | | | |
|---|---|---|---|
| 5,190,766 | 3/1993 | Ishihara | 604/22 |
| 5,267,985 | 12/1993 | Shimada et al. | 604/290 |
| 5,350,377 | 9/1994 | Winston et al. | 128/660.01 |
| 5,447,509 | 9/1995 | Mills et al. | 604/22 |
| 5,474,531 | 12/1995 | Carter | 604/22 |
| 5,556,372 | 9/1996 | Talish et al. | 601/2 |

*Primary Examiner*—John D. Yasko
*Assistant Examiner*—Ellen Tao
*Attorney, Agent, or Firm*—Michael J. Ward; Brian R. Woodworth

[57] ABSTRACT

The present invention relates to devices and methods for enhancing the rate and efficacy of permeation of a drug into and through skin and into the circulatory system utilizing ultrasound.

6 Claims, 2 Drawing Sheets

SONOPHORETIC DRUG DELIVERY SYSTEM

FIELD OF THE INVENTION

This invention is related to sonophoretic drug delivery systems.

BACKGROUND OF THE INVENTION

The majority of drugs in clinical use today are given either by injection or oral administration. Injections generally provide a fast, direct route to the bloodstream, whereas oral administration subjects the pharmaceutical agent to hepatic metabolism. Hepatic metabolism degrades the effectiveness of the pharmaceutical agents sometimes as much as 90% in some cases. The liver detoxifies drug molecules to a significant extent. As a result, a significant quantity may never reach the rest of the body due to the liver's detoxifying of the drug agent. Despite this drawback, oral administration still is the most preferred way of giving pharmaceutical drugs due to the ease of administration and the avoidance for the invasive techniques, such as injections.

Another, less common method of administration is by the use of ultrasonic vibration. An agent or drug may be driven through the skin, hair follicles, and sweat glands by the application of physical vibrations in the spectrum of Kilo-Hertz to MegaHertz. Traditionally, there has been a great degree of variation in efficiency and modes of transfer.

There are problems associated with delivering drugs by ultrasound. For example, one obstacle is delivering an agent or drug past the skin and into the circulation where it can produce its desired effect.

The human, adult skin structure can be broken down into three layers. The stratum corneum, which is part of the epidermal layer, is the first layer of skin defense against the exterior environment. The stratum corneum is capable of absorbing superficial trauma while still maintaining adequate protection against loss of water and invasion of microorganisms and other substances. The intercellular space of the stratum corneum is approximately 30% by volume and has lipids contained within which form transport barriers.

The second layer of the epidermal layer consists of epidermal cells bound together by tight junctions into a matrix. Between the junctions lie lipid filled extracellular spaces containing a host of cellular lymphocytic factors enzymes and other antimicrobial agents. The epidermal layer is the body's prime protective barrier. Its basal cells provide metabolic and additional water barrier functions. The epidermal barrier provides a formidable defense structure even in the absence of the stratum corneum, especially to water soluble agents that do not possess a lipid extracellular phase.

The innermost layer is the dermal layer. The dermal layer consists of basil germ cells positioned upon a basil membrane. Below the basil membrane are the majority of the capillary loops that comprise the terminal states of the microcirculation tree. Penetrating all three skin layers are numerous hair follicles in various growth states. The hair follicle growth stage correlates with the death of the follicle.

WO094/08655 describes an ultrasonic transducer assembly comprising a stimulus transducer and a second transducer. The stimulus transducer creates an ultrasonic wave in the skin which causes microscopic openings through which the second transducer drives the agent through the openings. The stimuli transducer provides a first frequency from about five KiloHertz (KHz) to one MegaHertz (MHz) range for a predetermined period of time while the second transducer provides a variable frequency ultrasonic pump impulses in the MHz range. The device requires two different types of transducers and for optimal performance requires the stimulus and second transducer to be placed at an angle to each other.

There remains a need for cost-effective, improved sonophoretic systems that can deliver an agent or drug to an individual in a controlled manner.

SUMMARY OF THE INVENTION

The present invention discloses devices and methods of a sonophoretic drug delivery system for delivering an agent or a drug to an animal. The sonophoretic drug delivery system comprises a power source, a generator, at least one transducer, a transmission line, a drug delivery site, and a control system for adjusting the delivery of drug to the animal.

DETAILED DESCRIPTION OF THE INVENTION

Figure 1:
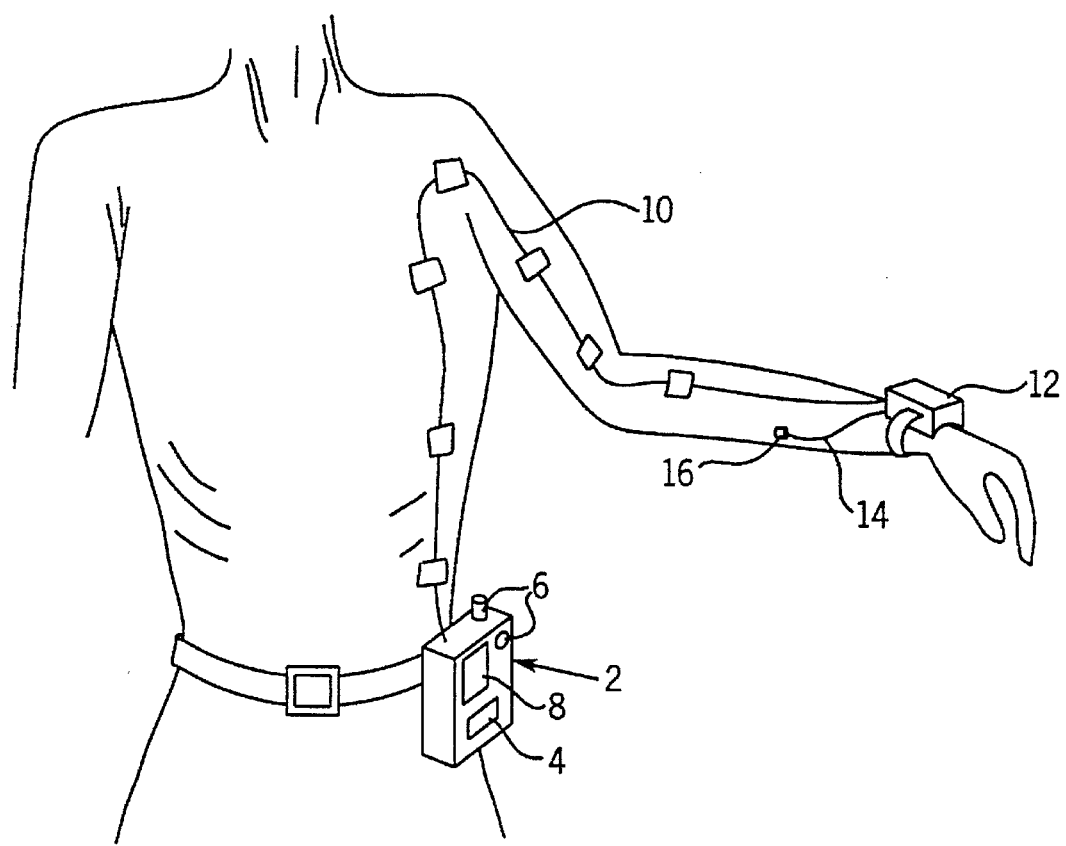
FIG. 1 depicts a patient wearing one embodiment of the sonophoretic drug delivery system of the present invention. The battery pack (2) includes at least one battery (4), a control system (6), and a generator (8); a wire (10); at least one transducer (12); an acoustic transmission line (14); and a reservoir (16) containing an agent or drug.

The present invention comprises a sonophoretic drug delivery system using ultrasound for transdermal penetration of an agent or drugs including pharmaceuticals, proteins, vitamins, inorganic and organic compounds as well as other substances, through the skin and into the circulatory system. The sonophoretic drug delivery system comprises a power source, a control system, at least one high frequency driver such as a generator, a transmission line such as an acoustic transmission line, and at least one ultrasonic transducer. In addition, the system may comprise an agent reservoir which may be loaded with the agent or drug of choice. In yet another alternative, the system may be operated by electrical batteries thereby making the device extremely portable.

The present invention relates to devices and methods for enhancing the rate and efficacy of permeation of a drug into and through skin and into the circulatory system. The present invention utilizes ultrasound to alter the passage of the molecules through the skin and into the circulatory system.

For purposes of this disclosure, the term "agent" or "drug" may be used interchangeably. More particularly the terms include, but are not intended to be limited to, antigens, haptens, antibodies, proteins, peptides, amino acids, carbohydrates, hormones, steroids, vitamins, lipids, nucleic acids, trace elements, drugs administered for therapeutic purposes, bacterium, viruses, and metabolites.

Ultrasound frequencies used by the sonophoretic drug delivery system of the present invention can be from about 20 KiloHertz to about 300 MegaHertz with intensities of from about 0 to about 4 watts per centimeter. Preferably, the sonophoretic drug delivery system of the present invention operates at a frequency from about 1 MHz to about 300 MHz. More preferably, the sonophoretic drug delivery system of the present invention operates at a frequency from about 10 MHz to about 300 MHz.

The control system turns the ultrasonic generator on and off and adjusts the frequency to optimize the delivery of the agent or drug to the patient. The control system is a basic electronic circuit well known to those skilled in the art and can be located in a device which houses the power source and generator or it can be at a separate location on the patient.

The sonophoretic drug delivery system of the present invention may be powered by an AC source such as an electrical cord which plugs into a typical electrical outlet. More preferably, the power source will be electrical batteries. Examples of batteries which can be used with the present invention include, but are not intended to be limited to, gel cell and rechargeable alkaline cell batteries (e.g., Duracell®). A battery pack can be conveniently placed anywhere on an individual. For example, the battery pack can be conveniently placed in a clothes pocket or clipped onto a belt or other clothing. In addition, the battery pack can be small and lightweight so that the power source does not unnecessarily burden the carrier. The battery pack may also house the control system and the generator.

Figure 2:
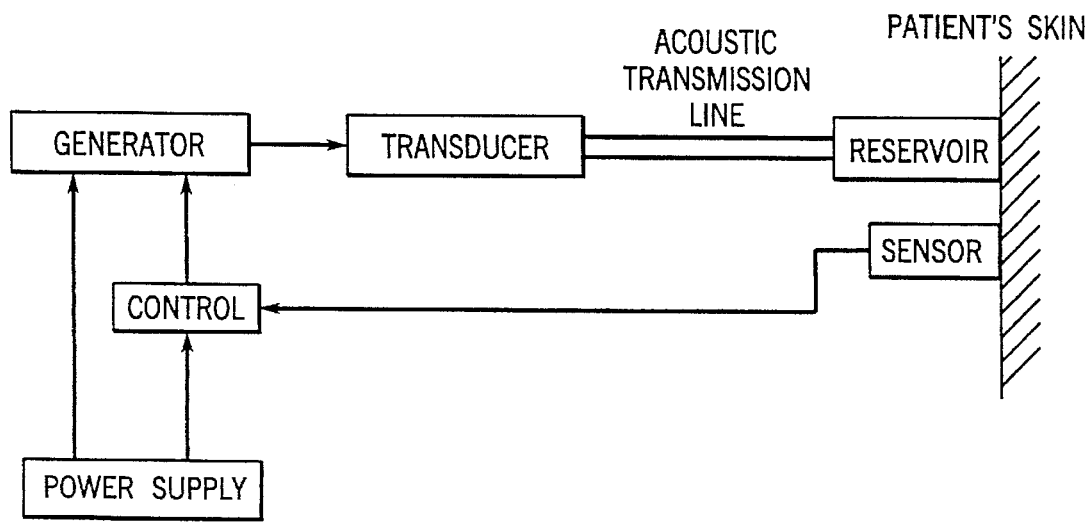
FIG. 2 depicts a schematic of one embodiment of the sonophoretic drug delivery system of the present invention having biological feedback into the control system.
Figure 3:
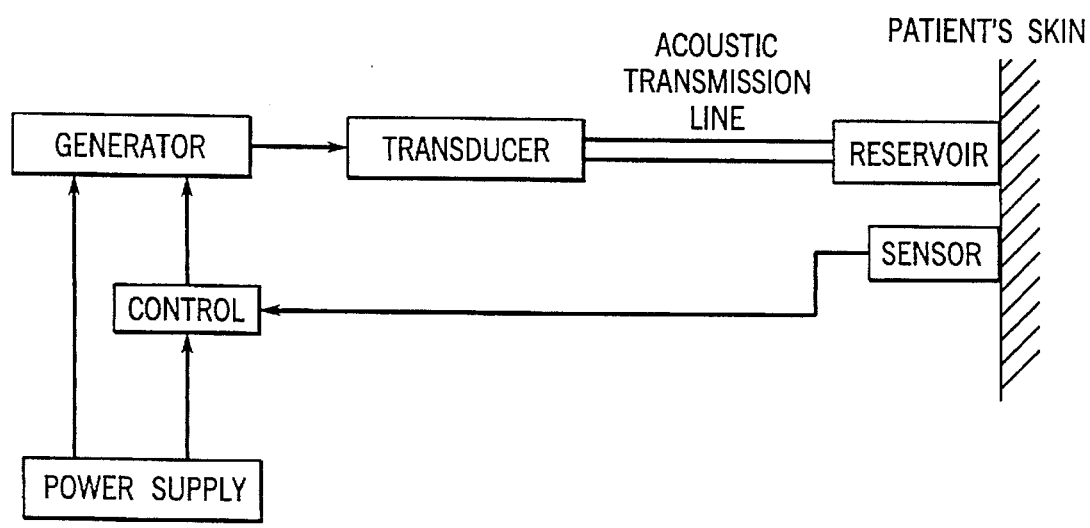
FIG. 3 depicts a schematic of one embodiment of the sonophoretic drug delivery system of the present invention having thermal feedback into the control system.

The power source powers the generator which typically generates a range of electrical signals which may be transmitted by a coaxial cable or other suitable wire to a transducer. As shown in FIGS. 2 and 3, the ultrasound generator propagates an electrical signal through a coaxial cable which carries the electrical impulse to the transducer. The coaxial cable is typically an insulated wire which is pliable and maneuverable. The insulated wire can be hidden under clothing if desired. The use of such coaxial cables are well known to those skilled in the art.

The generator may also comprise an amplifier to increase the input signal delivered to the transducer. For example, the amplifier receives the electrical signal from the ultrasound generator and amplifies the electrical signal. The amplified signal is then delivered to the transducer via electrodes which connect to the transducer. By applying a voltage across the electrodes, the transducer vibrates and emits ultrasonic mechanical energy. The ultrasonic mechanical energy is propagated from the transducer through the acoustic transmission line and eventually to the contact site. The use of generators is well known to those skilled in the art. Typically, the power source, control system, and generator may be housed in a single device although each may be housed separate from one another in the sonophoretic drug delivery system. The transducer may also be housed in the same device as the other components or housed separately.

The transducer may be a narrow band device such as a piezo-electric transducer. Piezo-electric transducers physically distort when stimulated by an electric charge. Connection of the transducer to an amplifier with the proper phase relationship can result in oscillations at the natural resonant frequency of the transducer (or a harmonic of it). The resonant frequency is largely determined by the dimensions of the material and its elastic modulus.

In a preferred embodiment, the transducer may be a wide-band device which is capable of vibrating in a wide range of frequencies. Some wide-band transducers can be excited by a tunable oscillator and amplifier over a wide range of frequencies. The advantage of wide-band transducers is the ability to sweep through a frequency range and operate at several frequencies. Different frequencies may be used to penetrate or move skin cells. The effect of the ultrasound on the drug may produce a "streaming" effect of agent or drug moving into the spaces between the cells and into the lower layers of the skin where it can be absorbed by the blood system. A number of different transducers are offered commercially by Ultran Transducer Company (Boalsburg, Pa.), Heat Systems Ultrasonics (Farmingdale, N.Y.), Precision Acoustic Devices (Fremont, Calif.), and Panametrics (Waltham, Mass.). "Streaming" is a phenomenon which occurs when an oscillation in a liquid or gaseous medium forces the medium molecules to move away from the source which results in a net flow of agent or drug away from the wave source. Such a phenomenon may be produced by sinusoidal and non-sinusoidal waves.

Another embodiment of the present invention includes a feedback phase-tracking loop to ensure that the frequency of the transducer matches the frequency of the amplified input signal. The feedback phase-tracking loop senses the response of the transducer to the frequency of the amplified signal and locks in on the frequency to give a maximum match. Applying an amplified signal to the transducer at a frequency other than the matched frequency may result in under-utilization of the amplified signal and its conversion to mechanical energy.

The ultrasound source can be transmitted along a fiber or rod by a transmission line such as an acoustic transmission line. The ultrasound is transmitted from the transducer along the acoustic transmission line to the drug delivery site. The drug delivery site may be either the drug reservoir or the skin/drug site where no reservoir is used. The proximal end of the transmission line is adjacent the transducer while the distal end is adjacent the drug delivery site. Acoustic transmission lines can be made of materials, such as glass fibers or polymers, which may transmit the ultrasound wave from the transducer to the site of drug delivery. The acoustic transmission line allows a remote location of the power source, control system, generator and transducer, thereby reducing the bulkiness of the system.

Yet another preferred embodiment of the present invention includes a face of the transducer having a concave surface while the other face comprises a convex surface. Simultaneous high intensity and high signal quality waves can be produced by placing a shaped ultrasound intensifier on such a geometrically focused transducer element. The intensifier abuts the concave surface of the transducer. The intensifier tapers from the concave surface to a narrow cross section. The width of the acoustic transmission line should be slightly larger than the region where the ultrasound vibrations converge. By placing a transmission line at the end of the intensifier, i.e., adjacent the narrow cross section of the intensifier or by making the acoustic transmission line an integral part of the intensifier, very high density bulk waves are propagated through the transmission line to the drug delivery site. In addition, a damping substrate may abut the convex surface of the transducer. U.S. Pat. No. 5,371,483 to Bhardwaj, hereby fully incorporated by reference, discloses such a transducer element having convex and concave faces.

An advantage of using sonophoresis to deliver drugs is that the rate and efficiency of transfer may be improved. Drugs associated with microspheres or microcapsules which would not pass through the skin and into the circulatory system may be transmitted through the skin when ultrasound is applied. By controlling the ultrasound frequency, intensity and time of exposure, the rate of transfer may be controlled.

As ultrasound is conducted via propagation of compressional waves through the skin, a coupling agent may be used with the present invention to allow for effective transmission of drug using ultrasound. Aqueous-based and oil-based coupling agents can be used with the present invention. For example, degassed water may be used as a coupling agent for transfer of mechanical energy from the device of the present invention into a patient due to the similarities in acoustic impedance between water and soft tissues. In addition, various gels and some creams are efficient coupling agents. Various aqueous based thixotropic gels are also suitable as coupling agents. Coupling agents, such as creams and thixotropic gels, are well known to those skilled in the art. The coupling agent may be loaded with substances such as antigens, haptens, antibodies, proteins, peptides, amino acids, carbohydrates, hormones, steroids, vitamins, lipids, nucleic acids, trace elements, drugs administered for therapeutic purposes, bacterium, viruses, antibodies, and metabolites.

The agent or drug to be delivered can be incorporated directly into a coupling agent or in the alternative, drug-coated or drug-loaded microcarriers may be delivered alone or incorporated into a coupling agent. The terms "microcarriers", "microspheres, and microcapsules" may be used interchangeably for the purposes of this disclosure. The terms include microcarriers which can have agent or drug bound to their surface, contained within the pores or cavities of the microcarriers, or encapsulated in a microcarrier. The rate of agent or drug release into the patient's circulatory system is controllable by the choice of microcarrier materials, such as the microcarrier's physical and chemical composition, as well as the drug's physical and chemical properties. Therapies using the sonophoretic drug delivery system of the present invention can include independently manipulating the physical and chemical compositions of both the microcarrier and the drug to optimize drug delivery.

The distal end of the transmission line relative to the transducer may contact the skin directly or indirectly. The distal end of the transmission line may contact the skin or coupling agent and/or microspheres directly where no drug reservoir is used. When a drug reservoir is used, the distal end of the transmission line may contact the drug reservoir which in turn contacts the patient's skin. The portion of the drug reservoir which contacts the patient's skin must be porous to the coupling agent and/or microcarriers upon ultrasonic stimulation from the transmission line. For sanitary purposes, it is only necessary to discard and replace the transmission line and drug reservoir when transferring the power source/control system/generator/transducer portion of the drug delivery system from one patient to another. Since the portion of the drug delivery system in contact with the patient is not transferred, such a system does not increase the risk of transferring diseases from one user to another and therefore does not require a sterilization process.

The agent or drug reservoir may be attached to the patient by a variety of means such as adhesives, tapes, synthetic and non-synthetic bands, and straps resembling wristwatch straps. For example, the reservoir may consist of an adhesive patch which contains an adhesive portion and a drug carrier portion.

The microcarriers used with the present invention can be loaded or coated with substances such as antigens, haptens, antibodies, proteins, peptides, amino acids, carbohydrates, hormones, steroids, vitamins, lipids, nucleic acids, trace elements, drugs administered for therapeutic purposes , bacterium, viruses, antibodies, and metabolites. The substances may be incorporated into microcarriers by imbedding, coating, or encapsulating the agent or drug. Upon microcarrier penetration into the dermis layer of the skin, drug release may be accomplished to produce the desired effect.

The type of release may be a factor in determining which microcarriers to use. For example, immediate versus sustained release have different requirements. If immediate release is desired, a reservoir type device encapsulated inside a film may be used (polyamide microcapsules inside a polyurethane matrix). For controlled release of bioactive substances, biodegradable or rupturable microcarriers which have penetrated the skin may be used(e.g., polyanhydride microspheres or microcapsules inside a polyanhydride matrix). The present invention is not intended to be limited to the microcarriers described herein since other microcarriers may be used as well. For example, homopolyanhydrides as described in U.S. Pat. No. 4,868,274 to Gupta, et al., hereby fully incorporated by reference, describes polyanhydrides that show an even rate of hydrolytic cleavage at different temperatures. More specifically, the homopolyanhydrides are synthesized by first forming a mixed anhydride of a desired carboxyaryloxyalkanoic acid monomer, an acid as prepolymer, and subsequently forming the homopolyanhydride by melt polycondensation of the prepolymer. The homopolyanhydrides of this invention can be mixed in the form of their melt with an agent or drug and formed into microspheres by slowly pouring the molten blend into silicone oil or other suitable oils which have been warmed to the same temperature as disclosed in Leong, et al, "Synthesis of Polyanhydrides: Melt-poly condensation, Dehydrochlorination and Dehydrative Coupling" published in Macromolecules, 20 (4), 705–712, (April, 1987), hereby fully incorporated as a reference. The homopolyanhydride in such microspheres acts as a controlled release agent for the active agent blended therewith as a result of its gradual hydrolytic cleavage under ordinary conditions.

Another embodiment of the present invention includes a biological feedback system to sense the amount of agent received by the body and control the ultrasound transmission of any further drug to be delivered. FIG. 2 depicts a schematic of the device including biological feedback. For example, a patient requiring insulin to control diabetes would have the level of blood sugar monitored and the introduction of insulin controlled to match the patient's insulin needs.

Yet another embodiment of the present invention includes a skin temperature sensor connected to the control system, as shown in FIG. 3, so as to limit the duration and amplitude of the applied ultrasound and prevent excessive temperature rise in the skin at the application site.

What is claimed is:

1. A sonophoretic drug delivery system for delivering an agent or a drug to an animal comprising:

a generator constructed to generate an electrical signal at a predetermined frequency, a cable having a first end portion connected to said generator and having a second end portion, a transducer connected to said second end portion of said cable, said transducer constructed to convert said electrical signal into mechanical energy, said transducer being a wide-band transducer, a transmission line having a proximal end portion and a distal end portion, said proximal end portion connected to said transducer, said transmission line constructed to transmit mechanical energy therethrough, said distal end portion of said transmission line constructed to deliver mechanical energy to a drug delivery site, and a control system for adjusting said electrical signal.

2. A sonophoretic drug delivery system of claim 1 wherein said frequency is from about 20 KiloHertz to about 300 MegaHertz range.

3. A sonophoretic drug delivery system of claim 1 wherein said frequency is from about 1 MegaHertz to about 300 MegaHertz range.

4. A sonophoretic drug delivery system of claim 1 wherein said frequency is from about 10 MegaHertz to about 300 MegaHertz range.

5. A sonophoretic drug delivery system of claim 1 further comprising an amplifier constructed to boost said frequency of said electrical signal from said generator.

6. A method for delivering an agent transdermally comprising the steps of:

providing a drug delivery system, said system comprising a generator constructed to generate an electrical signal at a predetermined frequency, a cable having a first end portion connected to said generator and having a second end portion, a transducer connected to said second end portion of said cable, said transducer constructed to convert said electrical signal into mechanical energy, a transmission line having a proximal end portion and a distal end portion, said proximal end portion connected to said transducer, said transmission line constructed to transmit mechanical energy therethrough, said distal end portion of said transmission line constructed to deliver mechanical energy to a drug delivery site spaced from said transducer, and a control system for adjusting said electrical signal;

providing an agent for transdermal delivery;

placing said agent in contact with a drug delivery site on an animal;

placing said distal end portion of said transmission line in contact with said agent; and activating said drug delivery system, whereby said agent is transdermally delivered at said drug delivery site.

* * * * *